(12) United States Patent
Brugger et al.

(10) Patent No.: US 7,901,579 B2
(45) Date of Patent: Mar. 8, 2011

(54) BLOOD TREATMENT DIALYZER/FILTER FOR PERMITTING GAS REMOVAL

(75) Inventors: James M. Brugger, Newburyport, MA (US); Martin Stillig, Dransfeld (DE)

(73) Assignee: NxStage Medical, Inc., Lawrence, MA (US)

( * ) Notice: Subject to any disclaimer, the term of this patent is extended or adjusted under 35 U.S.C. 154(b) by 125 days.

(21) Appl. No.: 12/432,507

(22) Filed: Apr. 29, 2009

(65) Prior Publication Data

US 2009/0229466 A1     Sep. 17, 2009

Related U.S. Application Data

(63) Continuation of application No. 11/163,708, filed on Oct. 27, 2005, now abandoned.

(60) Provisional application No. 60/622,863, filed on Oct. 28, 2004.

(51) Int. Cl.
*B01D 63/02* (2006.01)
*B01D 61/32* (2006.01)
*B01D 61/24* (2006.01)

(52) U.S. Cl. ............... 210/645; 210/321.71; 210/321.79; 210/646

(58) Field of Classification Search .................. None
See application file for complete search history.

(56) References Cited

U.S. PATENT DOCUMENTS

| | | | |
|---|---|---|---|
| 4,201,673 A | 5/1980 | Kanno et al. | |
| 4,218,313 A | 8/1980 | Aid et al. | |
| 4,498,990 A | 2/1985 | Shaldon et al. | |
| 4,617,161 A | 10/1986 | Rollins et al. | |
| 4,629,448 A | 12/1986 | Carlsson et al. | |
| 4,784,768 A | 11/1988 | Mathieu | |
| 4,976,685 A | 12/1990 | Block, Jr. | |
| 5,053,130 A | 10/1991 | Raff et al. | |
| RE33,932 E | 5/1992 | Fukasawa et al. | |
| 5,641,144 A | 6/1997 | Hendrickson et al. | |
| 5,643,190 A | 7/1997 | Utterberg | |
| 5,679,245 A | 10/1997 | Manica | |
| 5,698,090 A | 12/1997 | Bene et al. | |
| 5,702,597 A | 12/1997 | Chevallet et al. | |
| 5,725,776 A | 3/1998 | Kenley et al. | |
| 5,744,027 A | 4/1998 | Connell et al. | |
| 5,762,805 A | 6/1998 | Truitt et al. | |
| 5,776,345 A | 7/1998 | Truitt et al. | |
| 5,808,181 A | 9/1998 | Wamsiedler et al. | |
| 5,846,419 A | 12/1998 | Nederlof | |
| 5,863,421 A | 1/1999 | Peter et al. | |
| 5,871,694 A | 2/1999 | Beden et al. | |
| 5,885,454 A | 3/1999 | Yagihashi et al. | |
| 5,919,154 A | 7/1999 | Toavs et al. | |
| 5,951,870 A | 9/1999 | Utterberg | |
| 6,039,877 A | 3/2000 | Chevallet et al. | |
| 6,042,784 A | 3/2000 | Wamsiedler et al. | |

(Continued)

FOREIGN PATENT DOCUMENTS

WO    WO 2006/049822 A1    5/2006

*Primary Examiner* — Krishnan S Menon

(74) *Attorney, Agent, or Firm* — Mark A. Catan, Esq.; Miles & Stockbridge, P.C.

(57) ABSTRACT

A configuration of a blood microtubular filter/dialyzer used in many kinds of renal replacement therapy systems can provide a highly effective mechanism for removing air from the blood circuit of such systems. Air is removed from an outlet header space of the filter avoiding the need for a bubble trap or settling chamber such as a drip chamber.

17 Claims, 5 Drawing Sheets

U.S. PATENT DOCUMENTS

| | | |
|---|---|---|
| 6,071,269 A | 6/2000 | Schnell et al. |
| 6,579,253 B1 | 6/2003 | Burbank et al. |
| 6,641,731 B1 | 11/2003 | Heilmann et al. |
| 6,827,862 B1 | 12/2004 | Brockhoff et al. |
| 6,872,346 B2 | 3/2005 | Stillig |
| 6,955,655 B2 | 10/2005 | Burbank et al. |
| 6,979,309 B2 | 12/2005 | Burbank et al. |
| 7,297,255 B2 | 11/2007 | Stockbower |
| 2002/0056675 A1 | 5/2002 | Hegde |
| 2003/0010718 A1 | 1/2003 | Burbank et al. |
| 2004/0069709 A1 | 4/2004 | Brugger et al. |
| 2004/0127842 A1 | 7/2004 | Collins et al. |
| 2005/0000882 A1 | 1/2005 | Brugger et al. |
| 2005/0045540 A1 | 3/2005 | Connell et al. |
| 2005/0061740 A1 | 3/2005 | Felding et al. |
| 2005/0065459 A1 | 3/2005 | Zhang et al. |
| 2005/0090774 A1 | 4/2005 | Tonelli et al. |
| 2005/0251086 A1 | 11/2005 | Sternby |
| 2005/0274658 A1 | 12/2005 | Rosenbaum et al. |
| 2006/0091056 A1 | 5/2006 | Brugger |
| 2006/0091057 A1 | 5/2006 | Brugger et al. |
| 2006/0091058 A1 | 5/2006 | Brugger et al. |
| 2007/0102340 A1 | 5/2007 | Stillig et al. |
| 2008/0177215 A1 | 7/2008 | Brugger et al. |

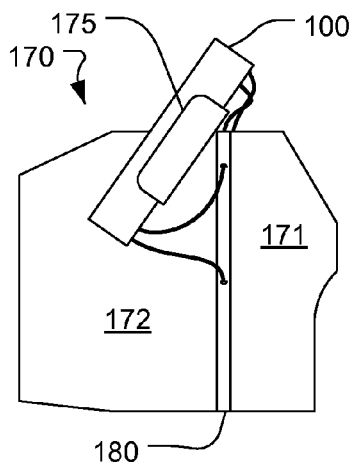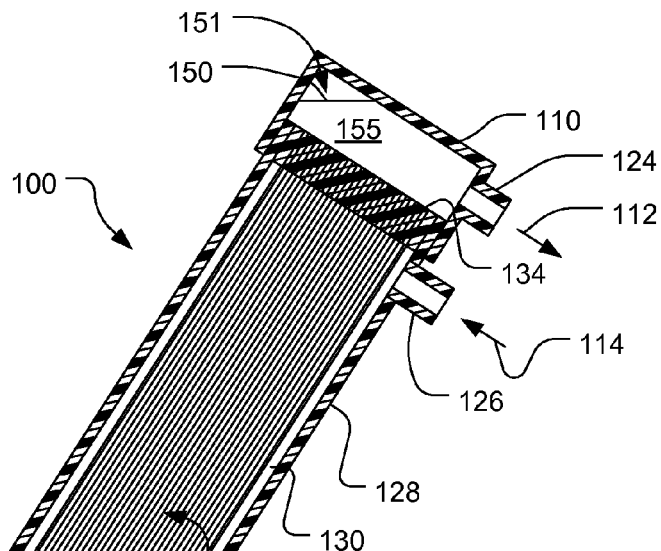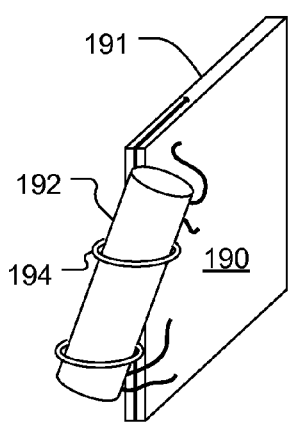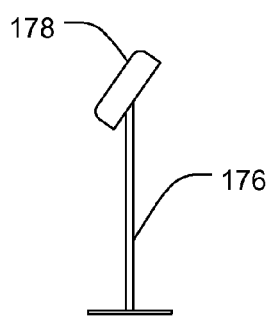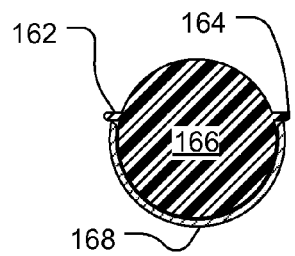
Fig. 2A
Fig. 1
Fig. 2B
Fig. 2C
Fig. 2D

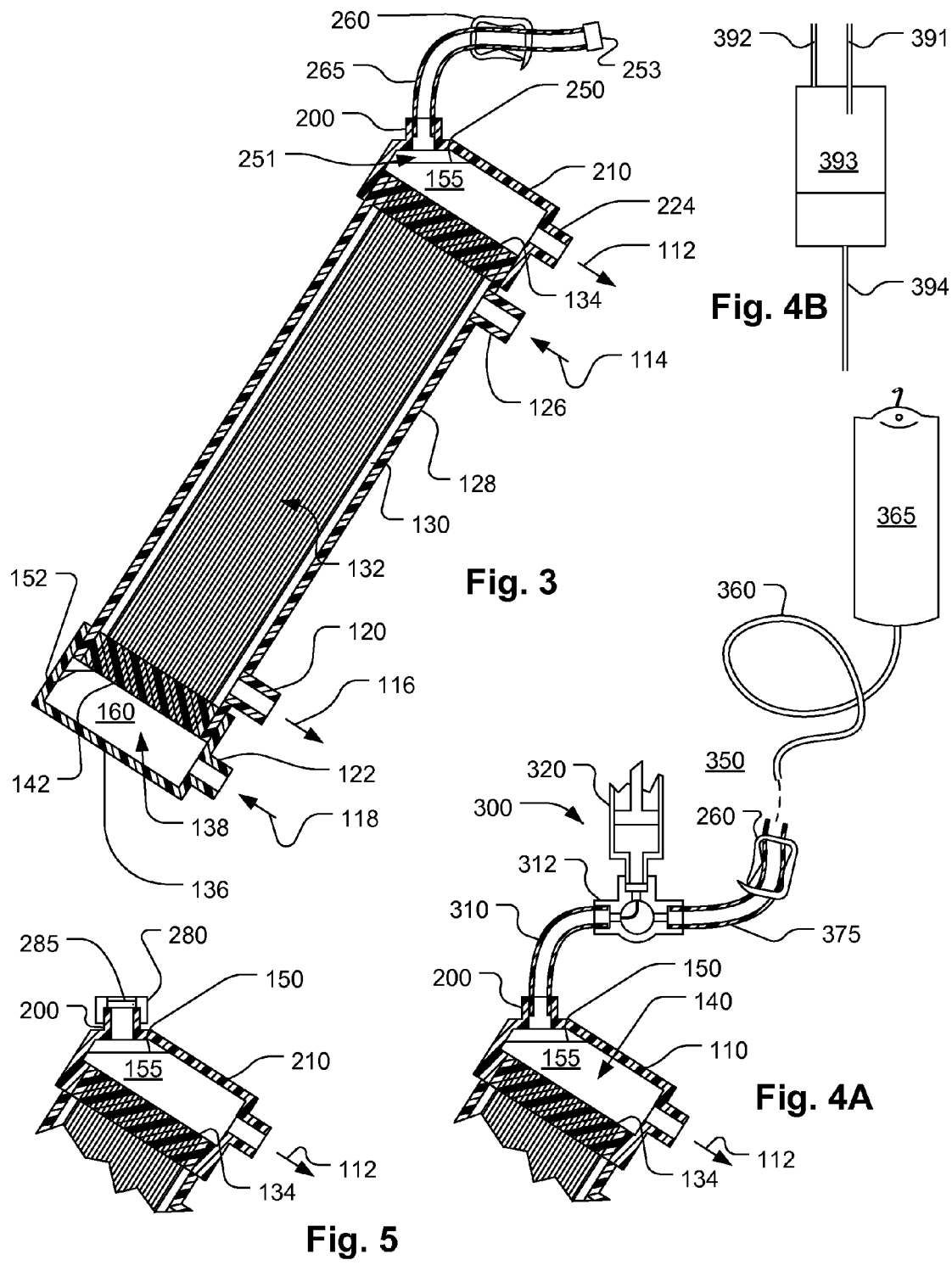

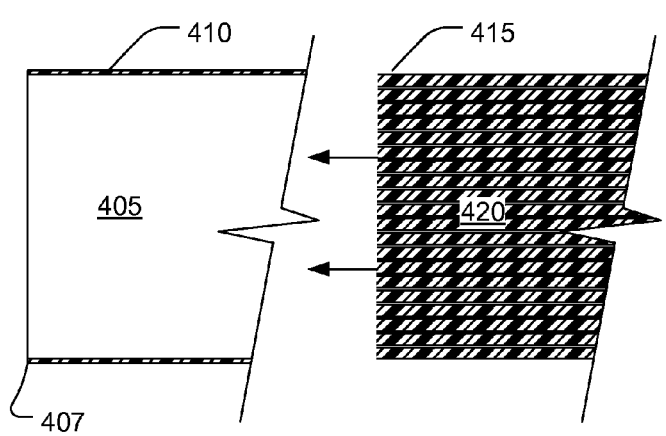
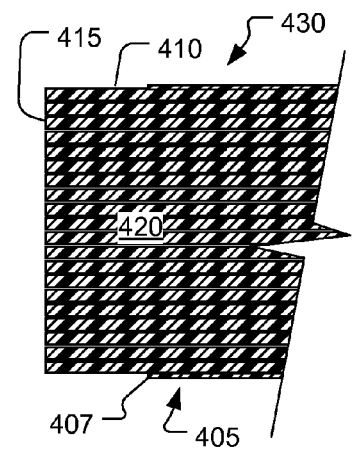
Fig. 6A  Fig. 6B
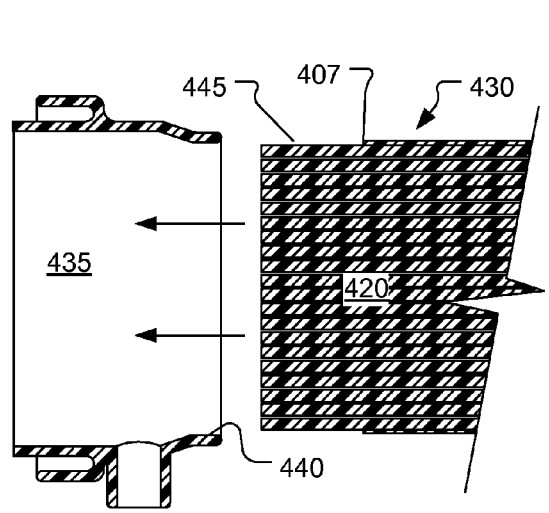
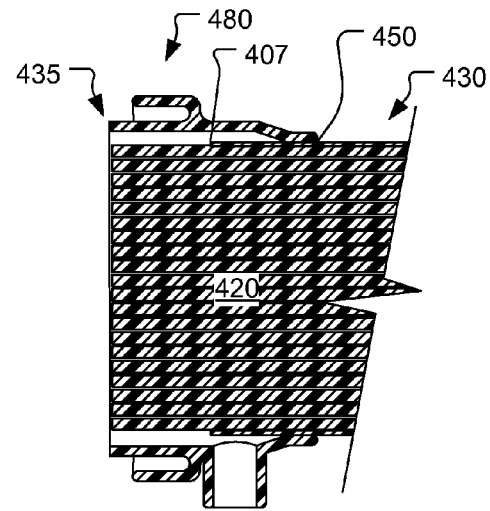
Fig. 7A  Fig. 7B

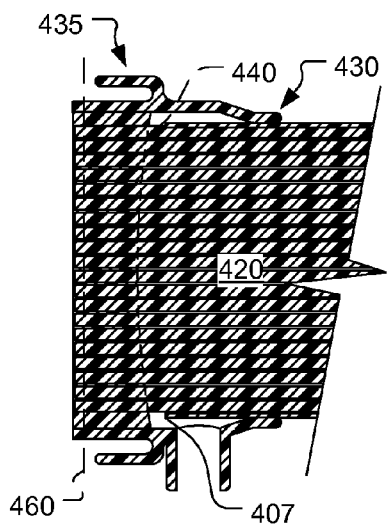 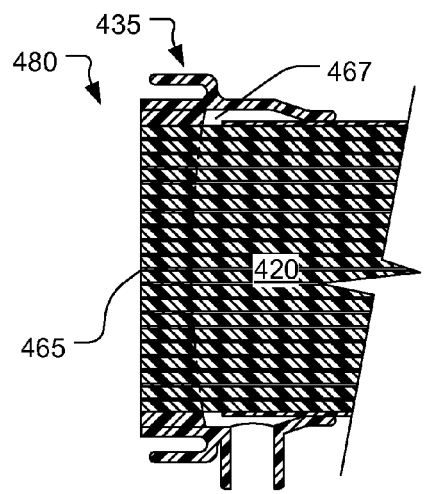
Fig. 8A                          Fig. 8B
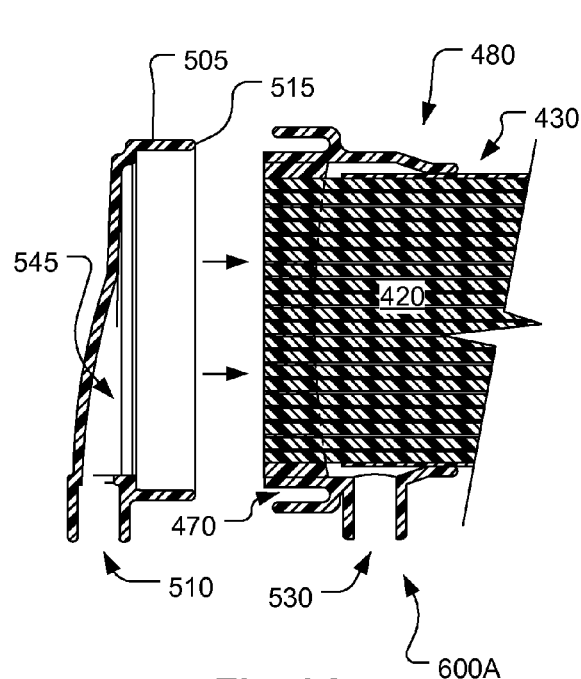 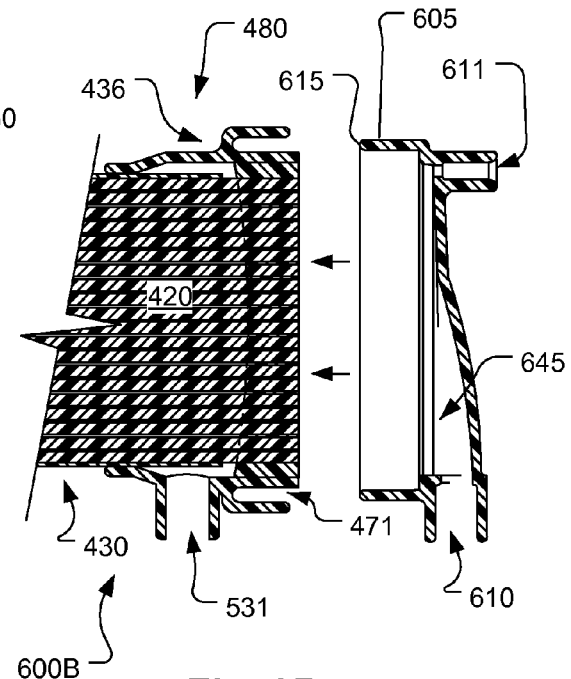
Fig. 9A                          Fig. 9B

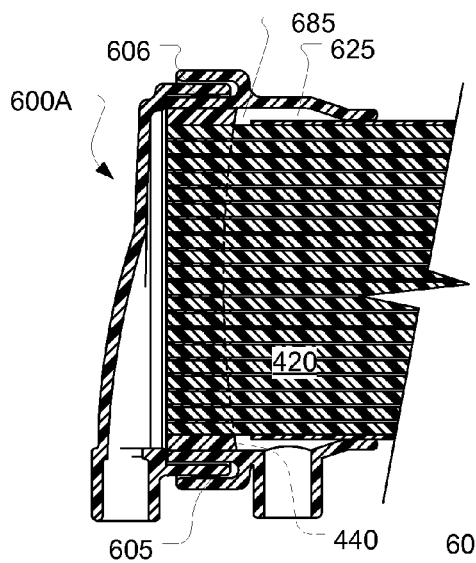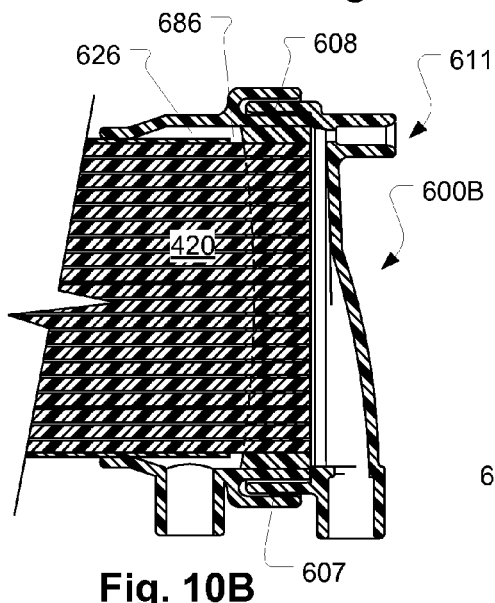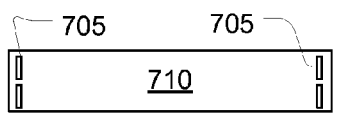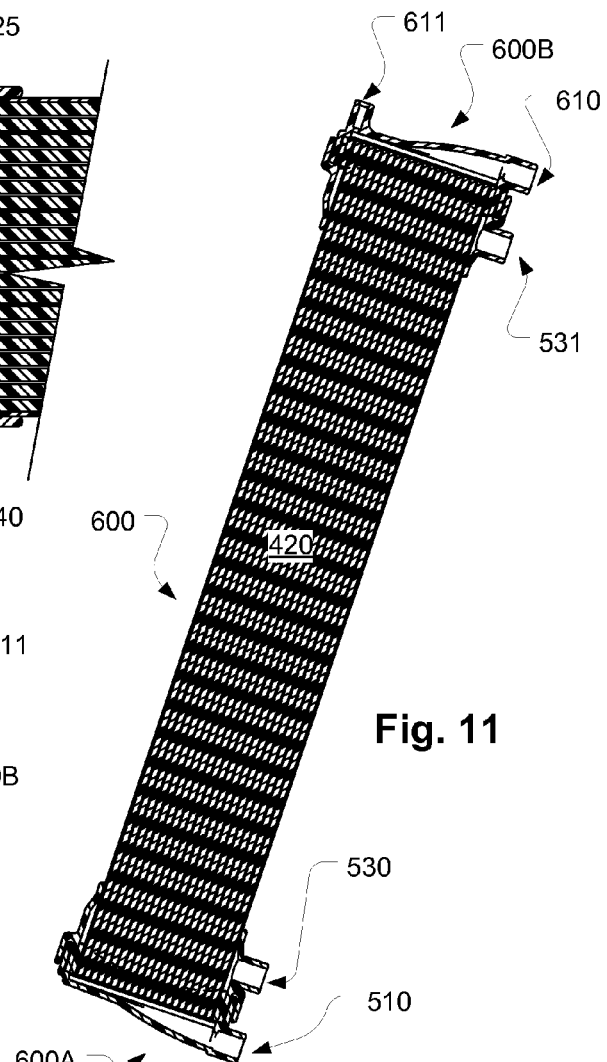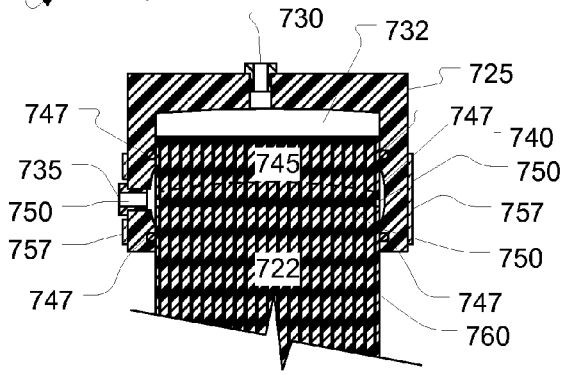

BLOOD TREATMENT DIALYZER/FILTER FOR PERMITTING GAS REMOVAL

CROSS REFERENCE TO RELATED APPLICATIONS

This application is a continuation of U.S. patent application Ser. No. 11/163,708, filed Oct. 27, 2005, now abandoned, which claims the benefit of U.S. Provisional Application Ser. No. 60/622,863, filed Oct. 28, 2004, both of which are incorporated by reference herein in their entireties.

BACKGROUND

One of the problems with fluid circuits in blood treatment systems is entrained air (bubbles) in treatment fluids, infusate, or blood. Treatment systems normally have air detectors to prevent air from being injected into a patient, either because a venous line carrying blood back to the patient contains air or because an infusate line, such as the replacement fluid line of a hemofiltration system, contains air. It is desirable for the air detectors to be made sufficiently sensitive to prevent the rare instances of long trains of air bubbles being injected into a patient. But sensitivity high enough to prevent long thin trains of bubbles may be high enough to alarm very small amounts of air which pose no risk. In other words, sensitive air detectors alarm on a lot of fall positives if they protect against all possible risks.

A prior art approach has been to remove as much air from a protected fluid circuit as possible. Putting air traps in fluid circuits, particularly blood lines, has drawbacks. Air-settling chambers necessarily involve stagnant flow, which creates a risk of forming clots (e.g., for blood) or sedimentation or other concentration of entrained material (e.g. medication).

Another prior art problem is stagnant flow in the headers of microtubular filter used for most dialyzers and hemofilters. This is a particular problem in the venous header where flow from many microtubules coalesces into a single slow moving flow.

The inventive embodiments provide various other features and advantages in addition to or in lieu of those discussed above and below. Many of these features and advantages are apparent from the description below with reference to the following drawing.

BRIEF DESCRIPTION OF THE DRAWINGS

FIG. 1 is a cross-section view of a filter usable in a variety of different types of blood treatment systems oriented to trap air in one or two header portions of the filter.

FIGS. 2A through 2C illustrate holders for use with the filter device embodiment described herein, including a particular example of application to a blood treatment device such as that of FIG. 1.

FIG. 2D illustrates an example of a holder feature to restrict orientations of a filter ensure that the filter is oriented with respect to the force of gravity.

FIG. 3 illustrates a filter similar to that of FIG. 1 but with a header port for removing air and/or disrupting or cleaning clots.

FIG. 4A illustrates an assembly for use with the port of FIG. 3 for removing air and/or disrupting or cleaning clots.

FIG. 4B illustrates a drip-chamber (or bubble trap) embodiment similar to the embodiment of FIG. 4A.

FIG. 5 illustrates a header cap with a hydrophobic membrane for automatically venting air.

FIGS. 6A through 9B illustrate a method for manufacturing a filter having a two-piece header caps that allow the use of a cylinder for a majority of the filter.

FIGS. 10A, 10B, and 11 illustrate the filter whose manufacture is described with respect to FIGS. 6A through 9B.

FIG. 12 shows an alternative configuration for connecting a dialysate manifold with a tubular body of the a filter according to an embodiment of the invention.

FIG. 13 illustrates a single element header component that uses a simple tube for the dialysate portion.

DETAILED DESCRIPTION OF THE DRAWINGS

FIG. 1 is a cross-section view of a filter usable in a variety of different types of blood treatment systems oriented to trap air in one or two header portions of the filter. A filter 100, which may be a dialyzer, hemofilter, hemodiafilter, or any other compatible blood treatment has a bundle of tubular media 132 connecting an arterial 160 and venous 155 head space which is isolated from a filtrate space 130. Blood flows through ports 122 and 124 in header caps 110 and 136 as indicated by arrows 118 and 112 into and out of the arterial 160 and venous 155 head spaces, respectively. A cylindrical filter body 128 encloses the filtrate space 130 and contains filtrate (e.g., dialyzer) ports 126 and 120. Arterial and venous headers 142 and 134 isolate the filtrate space 130 from the respective arterial 160 and venous 155 head spaces.

The orientation of the filter 100 with respect to the pull of gravity is shown with the understanding that gravity is assumed to pull down with respect to the profile orientation of the drawing page. If any air is entrained in the blood, it may settle in pockets 151 and 153 in the arterial 160 and venous 155 head spaces as indicated by air/liquid interfaces 152 and 150. The flow of blood through the arterial 160 and venous 155 head spaces is extremely slow due to the very small cross-sectional areas of the filter fibers in the bundle 132. As a result, the arterial 160 and venous 155 head spaces are an idea place for air to settle out. With the indicated orientation, with blood outlet 124 pointing down and away from the pocket 151. Since the blood moves at a very slow rate in the arterial 160 and venous 155 head spaces, there is little risk of reentrainment and air settles out very effectively.

Air trapped in pocket 153 may travel through filter fibers in bundle 132 up to venous head space 155 and accumulate in pocket 151. Since the pocket 153 is located near the top of the arterial head space 160, air will tend to travel up a few of the fibers closest to the top and collect in the pocket 151 without mixing in with blood. This keeps the vast majority of fibers filled with blood.

FIGS. 2A through 2C illustrate holder variations for the filter embodiments of the present patent disclosure. The variations are intended to illustrate examples and not intended to be comprehensive or limiting. In FIG. 2A, a holder 175 of a blood treatment machine orients a filter such as that of FIG. 1 and those of the further filter embodiments described below. The holder 175 may be attached at a base thereof (not shown separately) to a blood treatment machine 172 which may contain actuators, sensors, and control elements as well as a fluid circuit, here illustrated as a cartridge 180 enclosed between two parts 171 and 172 of the blood treatment machine 172. A filter 100 that is preconnected to the fluid circuit can easily be mounted in such an apparatus. The holder 175 may be articulating to allow for some movement or change of orientation of the filter 100 and is preferably a spring-tensioned clamp that allows for one-handed insertion of a filter 100. In an alternative embodiment, the holder 175 may be attached to the 180 cartridge such that its orientation is obtained when the cartridge 180 is positioned with respect to the blood treatment machine 170. In FIG. 2B, a holder 194 is integrated into a disposable unit 190 (such as the fluid circuit cartridge of FIG. 2A). For example, the holder 194 may be made of wire which is connected to a plastic panel support 191 of the disposable unit. Examples of such disposable units are disclosed in U.S. Pat. No. 6,955,655 for "Hemofiltration system" and U.S. Pat. No. 6,579,253 for "Fluid processing systems and methods using extracorporeal fluid flow panels oriented within a cartridge," each of which is hereby incorporated by reference as if full set forth in its entirety herein and U.S. patent application Ser. No. 10/650,935 published as US 2004-0069709, which is incorporated by reference above. The holder 194 supports a filter 192 such that when the disposable unit 190 is mounted, in a treatment device such as 170, the filter 192 is held at an angle as shown. Another alternative arrangement shown in FIG. 2C is to provide a separate support 178 that is attached, or attachable, to a support 176.

FIG. 2D illustrates an example of a holder feature to restrict orientations of a filter ensure that the filter is oriented with respect to the force of gravity. The view is a sectional view. In the example, the filter 166 has tabs 162 and 164 that prevent the filter 166 from being received fully within a flexible trough 168 which functions as a holder. This may be confirmed by inspection. The flexible trough 168 allows the filter 166 body to fit into it fully in only one orientation, the holder providing an urging force that keeps the filter 166 in place when inserted. Note that the example illustrated in FIG. 2D is only one of many devices that may be used to restrict the orientation of the filter when attached to a holder and is not intended to be limiting of the scope of any of the inventions described in the present disclosure.

FIG. 3 illustrates a filter similar to that of FIG. 1 but with a header cap 210 having an integrated header port 200 for removing air and/or disrupting or cleaning clots. Tubing 265 may be connected to the port and provided with a clamp 260. The clamp 260 may be released, at intervals, by an operator, to vent air from the air pocket 251 and re-engaged to prevent blood loss. The clamp 260 may be a normally-closed type clamp with a strong spring so that it reclamps tubing 265 when released. The tubing 265 may be capped with a microporous filter end cap 253 to prevent any contamination re-entering the blood in the venous head space 155. The entire assembly that includes the filter 100, tubing 265, and microporous filter end cap 253 may be fused, sealed, and sterilized as a unit. In addition the same may be fused, sealed and sterilized as a unit with an entire treatment circuit, combining it with the circuit described in U.S. patent application Ser. No. 10/650,935 published as US 2004-0069709, which is hereby incorporated by reference as if full set forth in its entirety herein. With this combination, the entire circuit may be isolated from contamination.

FIG. 4A illustrates an assembly 350 for use with the port of FIG. 3 for removing air and/or disrupting or cleaning clots. The port 200 has a tube 310 connecting the venous head space 155 with a multi-way valve (e.g., a stopcock as shown) 312. The multi-way valve 312 is further connected to a syringe 320 and tubing 375 connecting a supply of blood normal saline 375, heparin, drug, or other medicament (such as from a tube 360 and bag 365) such as anticoagulants, drugs, etc. The multi-way valve allows the syringe to be connected, in a first position, to draw saline from the source of saline 375 and, in a second position, to draw air from the venous head space 155. In the second position, saline may be pushed into the head space 155 to clear clots or for prophylaxis by injecting medicament, for example, an anticoagulant such as heparin. In an illustrative usage method, the multi-way valve 312 is set in the second position and air is drawn from the head space 155. Then it is set in the first position and saline is drawn into the syringe 320. Then the multi-way valve 312 is set in the second position again and saline (or saline and heparin) is injected into the venous head space 155. The apparatus including the multi-way valve 312, syringe 320, tubing 310, 375, 360 and clamp 260 may be pre-attached to the filter 100 and presterilized as a unit.

Note that besides using the multi-way valve and bag 365 to draw air from the header of a filter and inject medicaments into the filter header, the same devices may be used in connection with an air trap or drip chamber. Referring to FIG. 4B, a drip chamber 393 (which could also be a bubble trap or other similar device in which air may accumulate and possibly be vented), has an inlet 391 and an outlet 394. A connection 392 to the top of the drip chamber 393 may be connected to the line 310 shown in FIG. 4A and used in the manner described for removing air and/or injecting medicaments.

FIG. 5 illustrates a header cap 210 with cover 280 sealed to and covering the header port 200. The cover includes a hydrophobic membrane 285 that allows air in the head space 155 to vent automatically while preventing any contamination from entering.

Referring to FIGS. 6A and 6B, a method for manufacturing a filter design that incorporates features of the foregoing examples begins with the insertion of a filter fiber bundle 420 into a cylindrical tube 405 which forms part of a housing (discussed with reference to FIG. 11). The tube 405 is a straight tube with no other structural features, in the present example. As such, the tube 405 may be a thin walled structure allowing material to be saved. In addition, it may be made of a material that is not necessarily injection moldable, as filter housings generally are. A preferred material is glycol-modified polyethylene terephthalate, a copolyester (PETG) which may be a clear amorphous thermoplastic with high stiffness, hardness, and toughness as well as good impact strength. Other advantages of using a tube for the main part of the housing will become clear from the further description below. Note that in the drawing only one end of the tube is shown in the present and following figures, but a complementary operation may be performed at an opposite end of the tube 405 such that a mirror-image structure is obtained.

The filter fiber membrane bundle 420 may be inserted such that the fibers 415 extend beyond the end 407 of the tube 405 as indicated at 445. Referring now to FIGS. 7A and 7B, the resulting combination 430 of tube 405 and filter fibers 420 may be inserted in a dialysis cap 435. Note that the term "dialysis cap" is for convenience is not intended to limit the scope of the invention to the manufacture of a dialyzer. The outer surface of the tube 405 lies adjacent an inner annular surface 440 of the dialysis cap and a 450 bond is formed by thermal welding or sealing using adhesive, solvent, or filling type bonding agent such as urethane to form a completed structure 480. A symmetrical structure is formed at the opposite end so that both ends of the tube 405 have a dialysate cap 435.

Referring now to FIGS. 8A and 8B, potting caps (not shown) are placed over the ends of the structure 480 and the ends of the fiber bundle are potted as according methods that are known in the art of manufacturing filters. A preferred method of potting is described in U.S. Pat. No. 6,872,346 for a "Method and apparatus for manufacturing filters," which is hereby incorporated by reference as if fully set forth in its entirety herein. The result of potting is the creation of a sealed end of potting material indicated at 440 which, after hardening, is cut along a planar surface indicated at 460. The cut 460 is done in such a way that the end of the filter fibers 420 are open at the surface 465 forming. A portion of the dialysate cap 435 may be trimmed off in the process of cutting 460, as illustrated, although it will be apparent to those skilled in the art that this is not essential and instead, the fibers 420 could extend beyond the end of the dialysate cap 435 before potting such that the fibers 420 can be opened by cutting without cutting the dialysis cap 435. The completed end portion is shown in FIG. 8B, and as discussed, a symmetrical end portion may be completed at the opposite end (not shown here).

Referring now to FIGS. 9A through 11, the two ends 600A and 600B of a single tube structure are indicated. Respective blood caps 505 and 605 are fitted to the ends 600A and 600B of the structure 480. Each blood cap has a respective blood port 510, 610 and one of the blood caps has a secondary port 611 which will be recognized from the discussion of embodiments such as shown and discussed with respect to FIGS. 3 through 5. The blood caps 505 and 605 have respective header spaces 545, 645 that are preferably hydraulically shaped to ensure that no, or a minimal number of, dead (stagnant flow of blood) spaces arise when in use. In the embodiment shown, a rim 515 fits into an annular recess 470 (or rim 615 into annular recess 471). Prior to fitting the blood caps 505 and 605, a bead 605, 606, 607, 608 of adhesive or sealing material may be applied or injected in the annular recesses 470 and 471 to form a bond between the structure 480 and the respective blood caps 505 and 605. The bonding may be done by thermal, friction, solvent welding, compression bonding, or other technique. Dialysate ports 30 and 531 in the dialysate caps 435 and 425, respectively, allow dialysate to flow into and out of the space occupied by bundle 420 and in contact with the external surfaces of the filter bundle 420. For a hemofilter or other kinds of filters, such as sterile filters, reverse osmosis filters, ultrafilters, etc.; only one "dialysate" port would be required. Blood ports 510 and 610 in blood caps 505 and 605, respectively, supply blood into, and be recovered from, the header spaces 545 and 645, respectively. Air can be removed from air removal/access (secondary) port 611. As explained above, removal/access port 611 can also be used for injection of anticoagulants, drugs, or other medicaments.

As best seen in FIGS. 10A and 10B, a small gap 685, 686 is provided between the end 407 (FIGS. 6A, 7A, 8A) of the tube 405 (FIGS. 6A, 6B) and the surface of the potting 440 to allow dialysate to flow into the space occupied by the filter bundle 420. The dialysate (or filtrate, depending on the application) is distributed by an annular dialysate manifold space 626, 626. Referring momentarily to FIG. 12, it is noted that instead of providing for the gap 685, 686 in the manner described, the fiber bundle may be extended all the way to the end 407 of the tube 405 and openings 705 can be provided to perform the function of the openings 685, 686. The same features provide for extraction of filtrate or dialysate or other fluid depending on the application. FIG. 11 shows a complete filter unit. One of the benefits of the design is that it makes it possible to confine the capital expense associated with injection molding to the dialysate and blood header reducing first costs in new filter designs. In addition, the design allows the tubular portion to be lengthened and shorted without requiring major design and manufacturing changes. Note that although injection molding is not contemplated to be a requirement for the practice of the invention or all its embodiments, it is a preferred means for achieving the high precision and economies of scale for articles of manufacture such as dialyzers, filters, and hemofilters, as well as other applications of the disclosed embodiments.

Referring to FIG. 13, the benefit of using a tube for the filtrate/dialysate portion of the filter can be obtained by using a single-element header cap rather than separate "dialysate" and "blood" caps. In the example shown, a one-piece cap 725 has an annular dialysate manifold 740 that is sealed by O-rings 747 against the surface of a tube 760. A blood header space 732 is in communication with a blood port 730 and the dialysate manifold 740 is in communication with a dialysate port 735. Slits 750 (configured such as illustrated in FIG. 11) allow fluid communication between the dialysate manifold 740 and the external surfaces of the fiber bundle 733. A potting plug 745, in addition to performing its normal function, serves to reinforce the cylindrical structure of the tube 760 against the pressure of the O-ring 747 seals. In this embodiment, a tube is permitted to be used with a single-element cap 725 structure providing many of the benefits of the inventions discussed above.

A tension band 757 may be used to ensure a good seal and provide a final shape to the one-piece cap 725 if made of a somewhat compliant resin to allow it to be removed from an injection mold despite the recess defined by the dialysate manifold 740. Alternatively, the one-piece cap 725 may have a discontinuous dialysate manifold that allows it to be created without requiring the cap to yield, the cap could be machined rather than molded, or the cap could be made of two molded pieces that are assembled into a single cap. Many variations are possible.

It will be understood that while the invention has been described above in conjunction with a few exemplary embodiments, the description and examples are intended to illustrate and not limit the scope of the invention. That which is described herein with respect to the exemplary embodiments can be applied to the measurement of many different formation characteristics. Thus, the scope of the invention should only be limited by the following claims.

What is claimed is:

1. A method of removing gas from blood in a filter, comprising:

providing a microtubular fiber filter having a plurality of filter fibers with ends thereof opening into inlet header and outlet header spaces, the inlet header space having an inlet port and the outlet header having an outlet port and a gas release port;

the outlet port and the gas release port lying at opposite ends of the outlet header space;

the inlet header space and the outlet header space having inlet and outlet manifolds through which the filter fibers open, respectively, into the inlet and outlet header spaces;

positioning the filter such that in the inlet header space, blood flows at least partly upwardly through the inlet header space;

flowing blood through the inlet port into the inlet header space, through the plurality of filter fibers, into the outlet header space and out the outlet port;

flowing the blood along the inlet manifold so that fractions of the blood leave the inlet header space through the manifold to enter the filter fibers causing the remaining blood left behind to diminish in volume progressively along a length of the inlet manifold;

collecting gas in the inlet header space, conveying collected gas in a portion of the inlet manifold which feeds a subset of the filter fibers;

conveying gas through the subset of filter fibers into a portion of the outlet header space remote from the outlet port and adjacent the gas release port;

flowing blood along the outlet manifold toward the outlet port thereby accumulating blood in the outlet header progressively along a length of the outlet manifold as it enters the outlet header such that the volume of blood increases progressively from said portion of the outlet header space toward the outlet port;

the rate of flow of blood and the sizes and shapes of the inlet and outlet header spaces being such that the shear rate is sufficient to prevent any stagnant flow regions from arising in the inlet and outlet header spaces; and periodically releasing gas from said portion of the outlet header space.

2. The method of claim 1, wherein the filter has a longitudinal housing with a longitudinal axis, the method including supporting the filter such that the axis of the housing is at an angle with respect to the vertical.

3. The method of claim 1, further comprising connecting the filter to a blood circuit lacking a separate air trap to remove gas from blood.

4. The method of claim 1, further comprising connecting the filter to a blood circuit without a settling chamber for removing air from blood.

5. The method of claim 1, further comprising flowing dialysate in a space outside the filter fibers.

6. A method of removing gas from blood in a filter, comprising:

providing a microtubular fiber filter having filter fibers, an inlet header and an outlet header, the inlet header and the outlet header sealing, respectively, inlet and outlet header spaces where blood flows into and out of the filter fibers, respectively, the filter having a blood outlet port and a secondary port at opposite ends of the blood outlet header space, the secondary port having a microporous filter configured to prevent any contamination from entering the outlet header space;

supporting the filter at an angle such that the secondary port is at a highest point of the header space and the blood outlet port is lower than the secondary port;

passing blood into a blood inlet port of the inlet header space;

flowing the blood through the inlet header space and out of the inlet header space through the filter fibers such that air collects in a first pocket in the inlet header space and flows through some of the filter fibers to the outlet header space, the blood inlet port being located on a same side of the filter as the blood outlet port such that the first pocket forms opposite the inlet port;

flowing the blood through the filter fibers into the outlet header space and flowing the blood through the outlet header space to the blood outlet port, the inlet and outlet header spaces being hydraulically shaped such that the flowing the blood through the inlet header space and the flowing the blood through the outlet header space ensures that no stagnant flow of blood occurs;

permitting gas to collect in a second pocket in the outlet header space; and flowing dialysate in a space outside the filter fibers.

7. The method of claim 6, wherein the secondary port has a tube connected thereto and further comprising clamping the tube with a clamp and releasing the clamp at intervals during the flowing operations to permit gas to vent from the second pocket.

8. The method of claim 6, wherein the supporting the filter at an angle includes placing the filter in a holder that orients the blood inlet and outlet ports below the secondary port.

9. The method of claim 6, further comprising connecting the filter to a blood circuit such that the blood circuit lacks any separate gas trap configured for removing air from blood.

10. The method of claim 6, further comprising connecting the filter to a blood circuit such that the blood circuit has no settling chambers for trapping bubbles and is thereby devoid of stagnant flow regions.

11. The method of claim 6, further comprising sterilizing the filter, including the microporous filter, as a unit.

12. A method of removing gas from blood in a filter, comprising:

providing a microtubular fiber filter having a plurality of filter fibers, an inlet header and an outlet header, the inlet header and outlet header sealing, respectively, inlet and outlet header spaces where blood flows into and out of the filter fibers, respectively, the filter having a blood outlet port and a secondary port at opposite ends of the blood outlet header space;

passing blood into a blood inlet port of the inlet header space;

flowing the blood through the inlet header space and out of the inlet header space through the filter fibers;

flowing the blood through the filter fibers into the outlet header space and flowing the blood through the outlet header space to the blood outlet port, the inlet and outlet header spaces being hydraulically shaped such that the flowing the blood through the inlet header space and the flowing the blood through the outlet header space ensures that no stagnant flow of blood occurs;

permitting gas to collect in a pocket in the inlet header space and the outlet header space, which pockets are connected by a subset of the filter fibers thereby restricting the air from the remaining filter fibers;

releasing gas from the pocket through the secondary port at intervals during the flowing of blood through the filter; and flowing dialysate in a space outside the filter fibers.

13. The method of claim 12, wherein the secondary port has a tube and the releasing gas includes releasing a clamp on the tube.

14. The method of claim 12, further comprising supporting the filter at an angle by placing the filter in a holder that orients the blood inlet and outlet ports below the secondary port.

15. The method of claim 12, further comprising connecting the filter to a blood circuit such that the blood circuit lacks any separate air trap configured for removing air from blood.

16. The method of claim 12, further comprising sterilizing the filter, including a microporous filter on the secondary port, as a unit.

17. The method of claim 12, further comprising providing on the secondary port a microporous filter configured to prevent any contamination from entering the outlet header space.

* * * * *